(12) United States Patent
Henderson

(10) Patent No.: US 11,974,944 B2
(45) Date of Patent: May 7, 2024

(54) EYE DROPPER DEVICE

(71) Applicant: J4J, LLC, Twin Falls, ID (US)

(72) Inventor: Jared R. Henderson, Twin Falls, ID (US)

(73) Assignee: J4J, LLC, Twin Falls, ID (US)

( * ) Notice: Subject to any disclaimer, the term of this patent is extended or adjusted under 35 U.S.C. 154(b) by 0 days.

(21) Appl. No.: 18/155,636

(22) Filed: Jan. 17, 2023

(65) Prior Publication Data

US 2023/0225902 A1 Jul. 20, 2023

Related U.S. Application Data

(60) Provisional application No. 63/370,345, filed on Aug. 3, 2022, provisional application No. 63/300,211, filed on Jan. 17, 2022.

(51) Int. Cl.
*A61F 9/00* (2006.01)

(52) U.S. Cl.
CPC .................... *A61F 9/0008* (2013.01)

(58) Field of Classification Search
CPC ...... A61F 9/0008; A61F 9/0026; A61F 11/00; B01L 3/027
See application file for complete search history.

(56) References Cited

U.S. PATENT DOCUMENTS

| | | | |
|---|---|---|---|
| 2,626,606 A | 1/1953 | Campbell | |
| 3,788,528 A | 1/1974 | Ogle | |
| 4,471,890 A | 9/1984 | Dougherty | |
| 4,605,398 A | 8/1986 | Herrick | |
| 4,927,062 A | 5/1990 | Walsh | |
| 5,007,905 A | 4/1991 | Bauer | |
| 5,040,706 A | 8/1991 | Davis | |
| 5,059,188 A | 10/1991 | Goddard | |
| 6,041,978 A | 3/2000 | Hagele | |
| 6,197,008 B1 | 3/2001 | Hagele | |
| 6,869,421 B2 | 3/2005 | Hanley | |
| 7,527,613 B2 | 5/2009 | Gaynes | |
| 7,563,256 B2 | 7/2009 | Hearne | |
| 7,758,553 B2 | 7/2010 | Poisson | |
| 7,846,140 B2 | 12/2010 | Hagele | |
| 8,287,505 B2 | 10/2012 | Pine | |

(Continued)

FOREIGN PATENT DOCUMENTS

| | | |
|---|---|---|
| JP | 2019166228 A | 10/2019 |
| WO | 2005074543 A2 | 8/2005 |
| WO | 2014055676 | 4/2014 |

*Primary Examiner* — Benjamin J Klein
*Assistant Examiner* — Hans Kaliher
(74) *Attorney, Agent, or Firm* — Scott D. Swanson; Shaver Swanson

(57) ABSTRACT

An improved eye drop dispenser apparatus having a suspension frame or tip configured for retention of an eye drop. The eye drop is suspended on the suspension frame by surface tension and adhesion forces of the liquid, with the suspension frame held proximate to the eye of a user or patient. The eye drop contacts the eye, with the surface tension causing the drop to transfer to the eye. The dispenser apparatus is configured to connect to an eye drop reservoir either by positioning into the opening in the eye drop bottle in a neck of the bottle, by positioning over the exterior of the neck of the eye drop reservoir, or by positioning over a pre-existing dispenser tip of the eye drop reservoir.

16 Claims, 16 Drawing Sheets

(56) References Cited

U.S. PATENT DOCUMENTS

| | | |
|---|---|---|
| 8,496,635 B2 | 7/2013 | Katayama |
| 9,681,729 B2 * | 6/2017 | Geiger .................. A61F 9/0008 |
| D852,351 S | 6/2019 | Alvino |
| 10,695,216 B2 | 6/2020 | Song |
| 2005/0049562 A1 | 3/2005 | Cress |
| 2006/0116649 A1 * | 6/2006 | Hagele .................. A61F 9/0008 604/295 |
| 2010/0006600 A1 | 1/2010 | Dascanio |
| 2016/0270956 A1 | 9/2016 | Lin |
| 2017/0266043 A1 | 9/2017 | Orloff |
| 2019/0060111 A1 * | 2/2019 | Lin ....................... A61F 9/0026 |
| 2021/0030589 A1 * | 2/2021 | Enemark ............... A61F 9/0008 |
| 2021/0221575 A1 | 7/2021 | Pharma |
| 2022/0388737 A1 * | 12/2022 | Gamboa Burgos .... B65D 47/18 |

\* cited by examiner

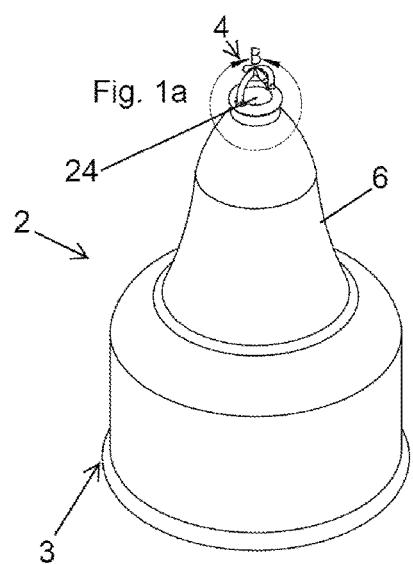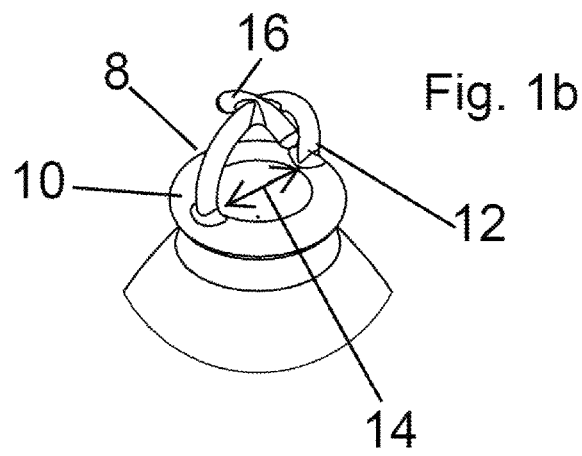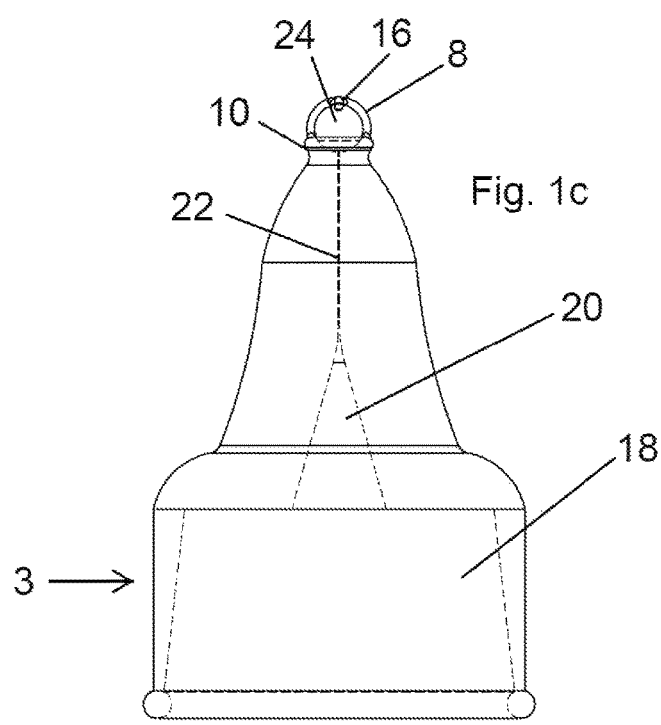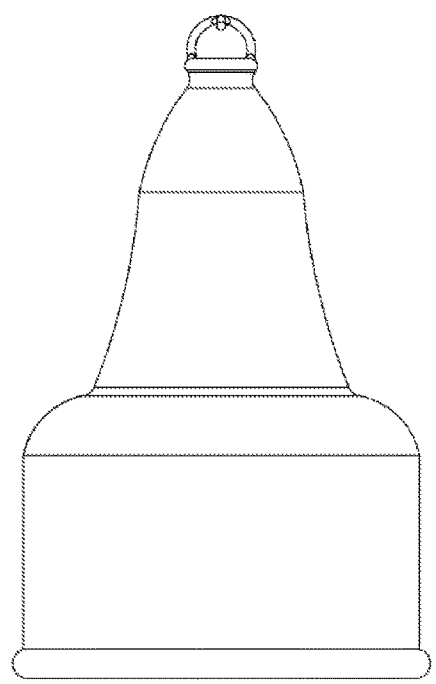

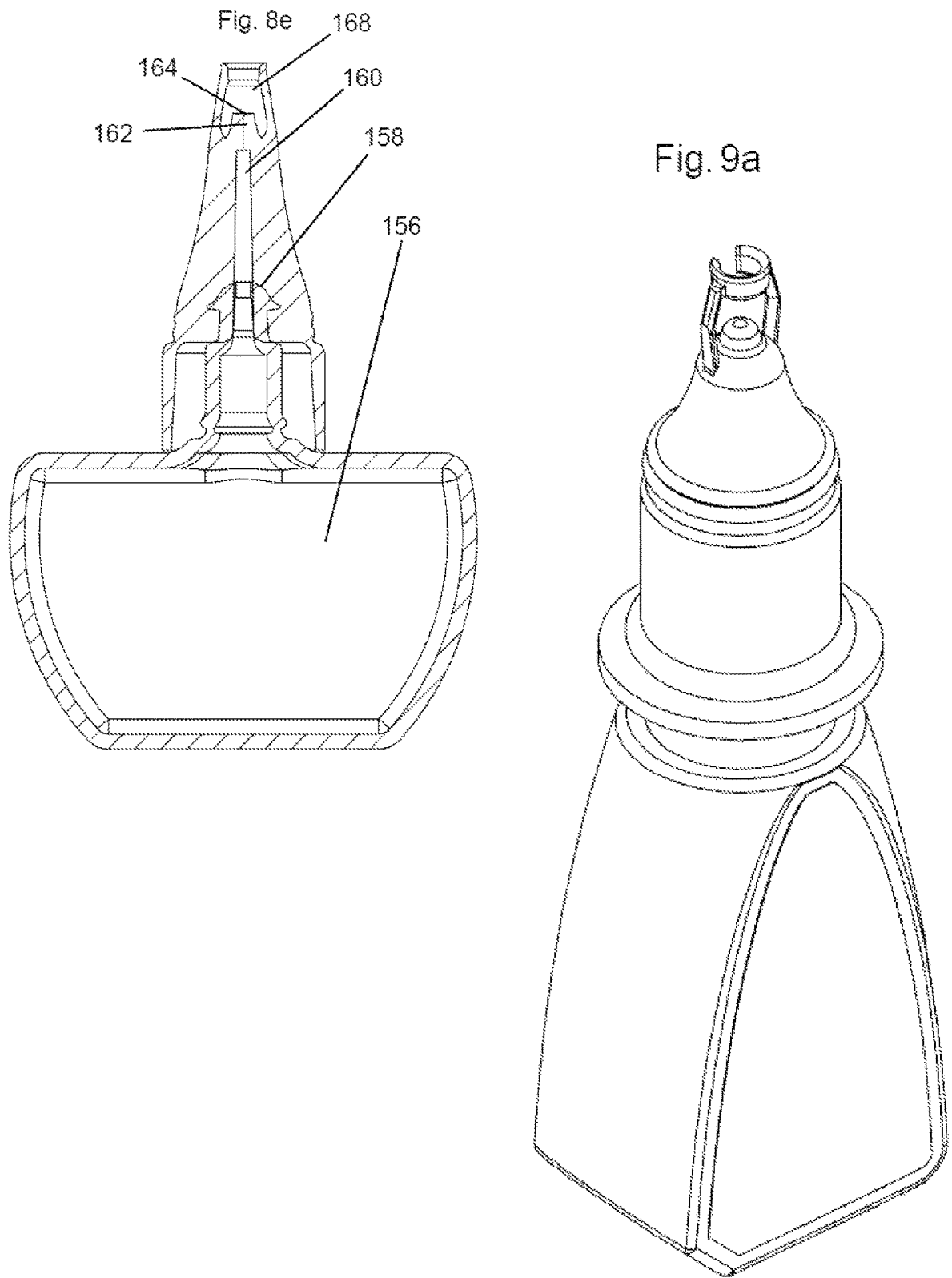

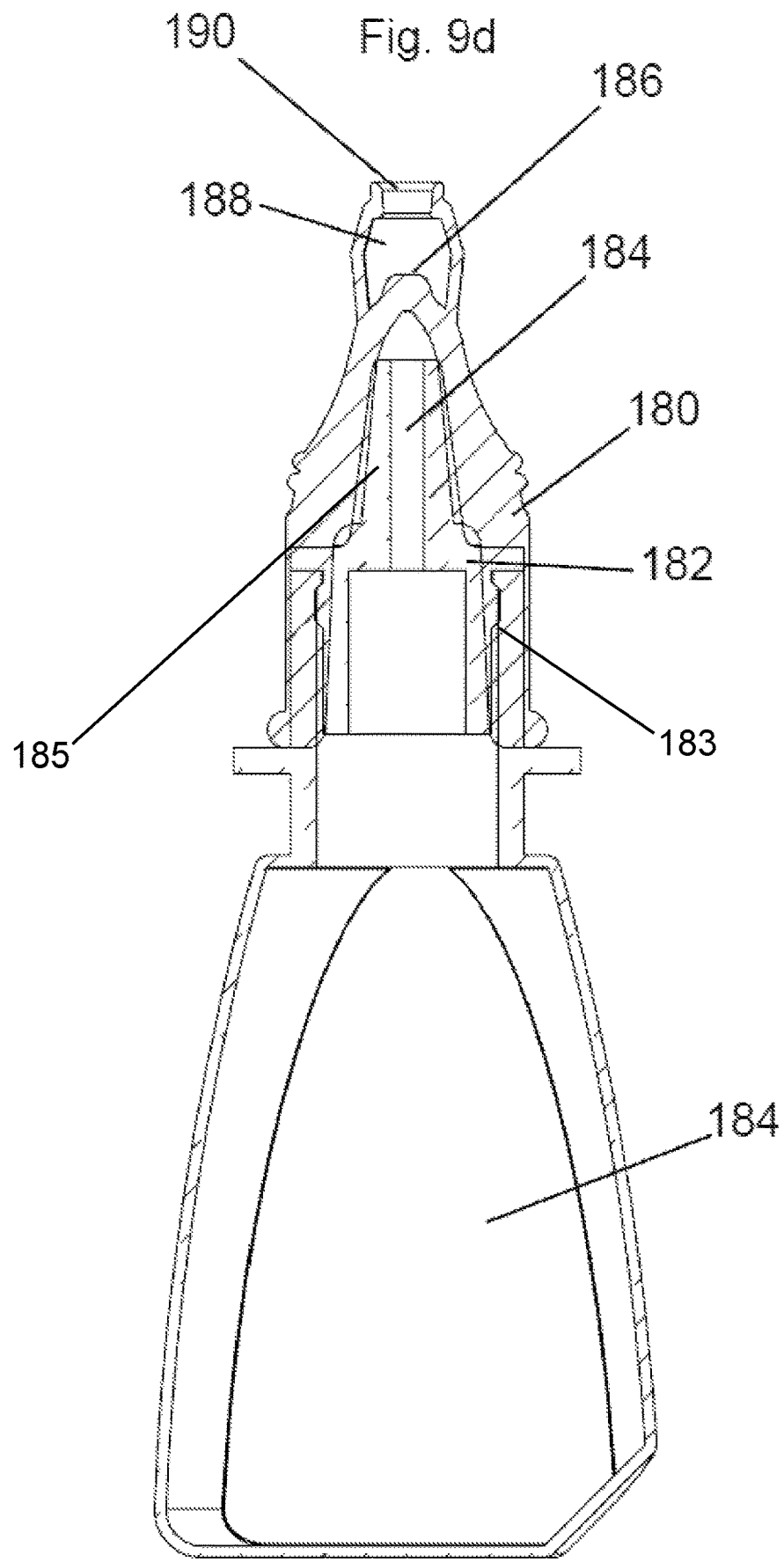

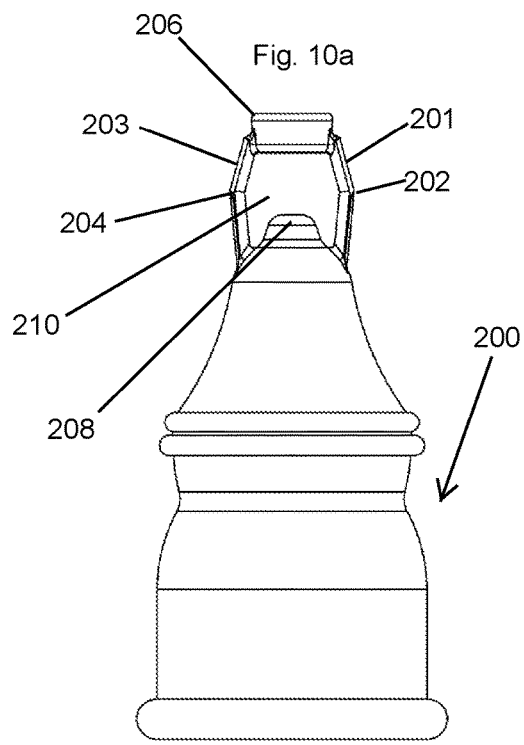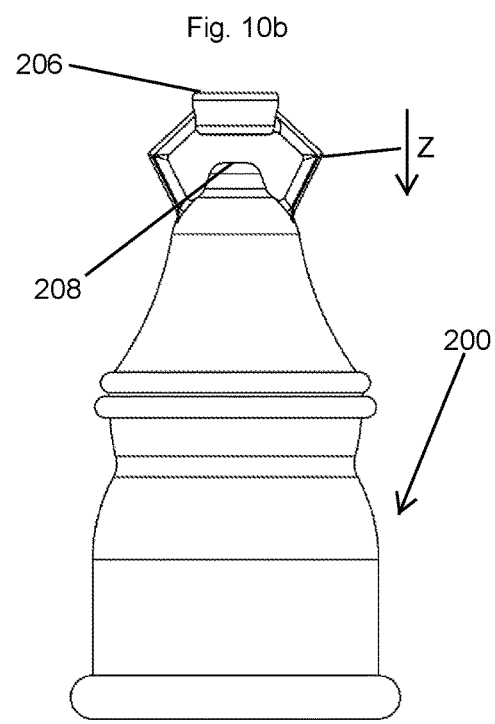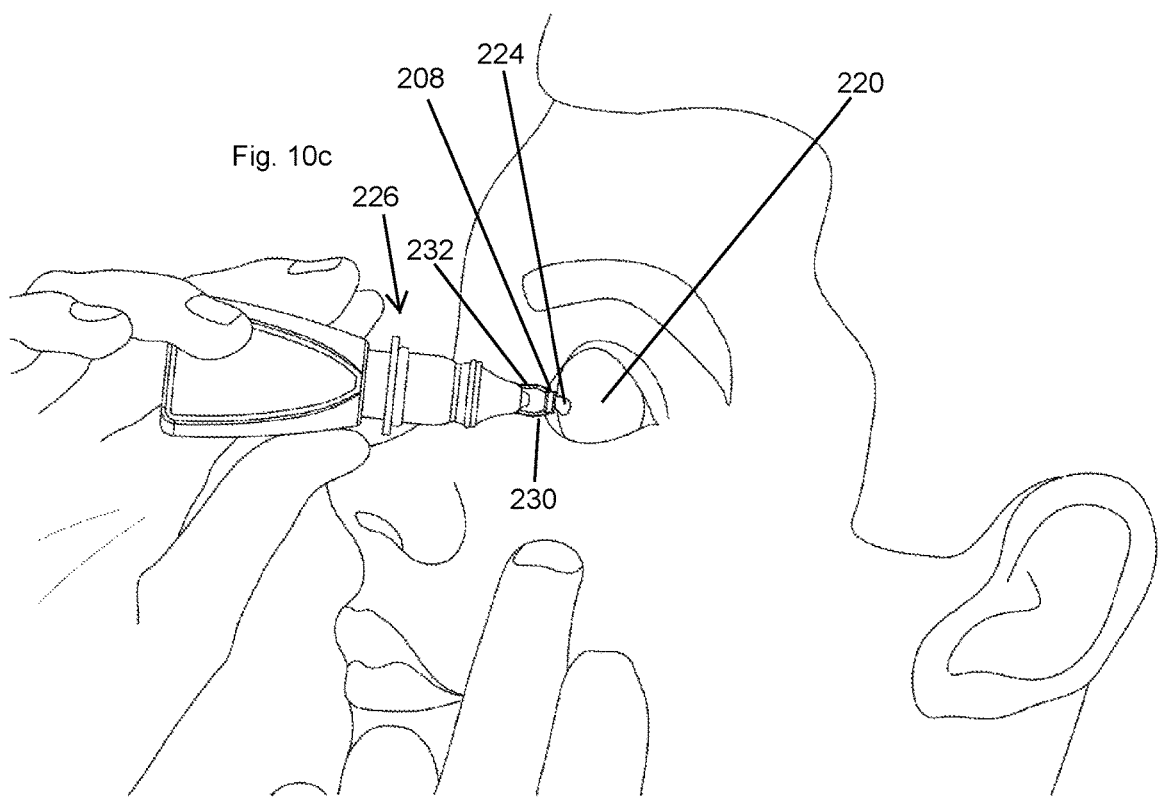

EYE DROPPER DEVICE

CROSS-REFERENCE TO RELATED APPLICATIONS

This application claims the benefit of U.S. Provisional Patent Application No. 63/300,211, filed Jan. 17, 2022, and U.S. Provisional Patent Application No. 63/370,345, the disclosure of each of which is incorporated by reference.

FIELD OF THE INVENTION

The disclosure relates to the field of dispensing liquid eye drops. Particular embodiments relate to an applicator that can separate a portion of liquid from reservoir in a manner that retains the integrity of the remaining liquid. Further the disclosed embodiments will allow user to dispense and transfer a droplet or quantity of liquid in a controlled fashion using but not limited to the properties of liquid cohesion, adhesion and surface tension to the structural components of the device. Further the disclosed embodiments will temporarily suspend the desired droplet or quantity of liquid on the terminal end of the device in a manner to facilitate easy safe transfer to the eye surface.

BACKGROUND OF THE INVENTION

Instillation of eye drops from a bottle onto the surface of the eye has always been difficult at best. The current convention is to hold an eye dropper above the eye and in some fashion make a droplet break off of the container and fall by gravity onto the surface of the eye or inside the eyelid. This conventional method presents many hazards including, apparatus impacting the eye surface, reservoir and dispensing tip contamination, medication misplacement outside of the eye, waste by applying multiple drops among other problems. Technical limitations of the user exacerbate an already cumbersome process. Those with visual impairment, tremor, impaired dexterity, and the elderly or otherwise limited sometimes forgo needed eye drops because of the difficulty of the process.

Even aided by a mirror liquid instillation is somewhat of a blind endeavor adding to existing hazards. The closer to the eye the dropper is held to the eye the better chance of getting the liquid in the appropriate location, but this fact presents a hazard to critical eye structures. Many medical studies have verified that the tip of the eye dropper often comes into contact with structures such as the eyelid, eye surface or face where it can be contaminated with bacteria. This becomes problematic when bacteria now present on the tip of the device are transferred to the reservoir through the existing open conduit. This happens when the force which initially pushes out the droplet is withdrawn and the resulting negative pressure in the reservoir and liquid is aspirated up from the tip into the reservoir. These facts present juxtaposition for the user, making it necessary to choose either to hold the dropper closer to minimize misplacement and risk contact with the eye and/or contamination of the contents, or to hold it further away and risk missing the eye. Having objects in very close proximity to the eye presents an obvious injury hazard especially if these objects are rigid or otherwise less conformal than the surface of the eye.

Devices exist that can temporarily hold a droplet on a separate apparatus from the eye dropper and facilitate transfer to the eye surface. This too can be cumbersome because it takes coordination and fine dexterity to "load" the droplet on this apparatus and then transfer it to the eye surface. Some frustrated users have also saturated Q-tips with eye medication in an attempt to transfer the liquid with less mess.

Current eye droppers function according to "the bombing method" where an eye drop falls from above the eye, accelerates by gravity, and contacts the corneal or other eye surface transferring force to it. Hitting the corneal surface is problematic because it's very sensitive and can stimulate a squinting reflex. When triggered by falling eye drops this reflex decreases the holding space on the surface of the eye and forces the eye drops that were newly instilled off of the eye surface before the purpose of administration is achieved. This is often evidenced as "tearing" that occurs after an eye drop is instilled. Most of the liquid running out of the eye after instillation is the liquid that has just been instilled. Eye drops running down the face have obvious cosmetic, financial and medical implications. Many aids and devices exist to help "aim" the eye drops yet again prove that instillation of eye drops is difficult at best even while attempting administration under limited visualization. The components of this apparatus will allow the user to bypass a gravity propelled system eye drop delivery and retain control of the liquid until delivery at the eye.

BRIEF DESCRIPTION OF DRAWINGS

FIG. 1a is a perspective view of an embodiment of an eye dropper dispenser attachment configured to suspend a drop of liquid for placement in a user's eye.

FIG. 1b is detail view of the tip of the attachment of FIG. 1a at line 1b of FIG. 1a.

FIG. 1c is a side isometric view of the embodiment shown in FIGS. 1a-1b using dashed lines to illustrate the internal configuration of the embodiment.

FIG. 1d is a first side isometric view of the embodiment shown in FIGS. 1a-1c.

FIG. 2b is an isometric view of the embodiment of FIG. 2a.

FIG. 4b is an isometric view of the embodiment of FIG. 4a.

FIG. 4c is a second isometric view of the embodiment of FIG. 4a.

FIG. 6b illustrates an isometric view of the embodiment of FIG. 6a.

FIG. 8e illustrates a section view along line A of FIG. 8d.

FIG. 9a illustrates an alternate embodiment of an assembly of an eye drop attachment positioned over the preexisting dispenser tip of an eye drop dispenser.

FIG. 9b illustrates an isometric view of the assembly of FIG. 9a.

FIG. 9d illustrates a section view along line B of FIG. 9c.

FIG. 10a illustrates a further embodiment of a tip having support arms configured for deflection with support arms in an extended position.

FIG. 10b illustrates the embodiment of FIG. 12 having support arms in a deflected position.

FIG. 10c illustrates an embodiment of the invention being used to dispense an eye drop into the eye of a user.

FIG. 11b illustrates a detail view of the dispensing end of the reservoir and dispensing attachment of FIG. 11a.

SUMMARY

Figure 1E:
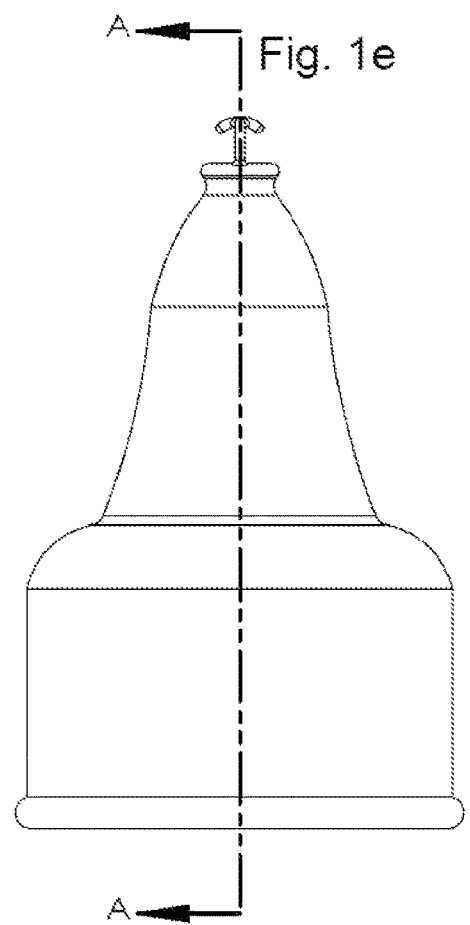
FIG. 1e is a second side isometric view of the embodiment shown in FIGS. 1a-1c.

While the presently disclosed inventive concepts are susceptible of various modifications and alternative constructions, certain illustrated embodiments thereof have been shown in the drawings and will be described below in detail. It should be understood, however, that there is no intention to limit the inventive concepts to the specific form disclosed, but, on the contrary, the presently disclosed and claimed inventive concepts is to cover all the modifications, alternative constructions, and equivalents falling within the spirit and scope of the inventive concepts as defined there in.

Embodiments of the disclosed dropper device use an elastomeric material as its base component such as silicone, rubber or latex (but not limited to these materials) which will allow it to stretch and "form fit" over existing eye dropper bottles in a universal fashion. This allows the dropper device to readily adapt to different size containers and geometry of dispensers. The elasticity of these materials will also be utilized to form a seal between the device and the existing eye dropper bottle dispensing apparatus or reservoir. Elasticity of the elastomer could be changed as desired to increase the functionality of the product. For instance, Shore 25A could be utilized but if more elasticity was desired Shore 20A could be used. An alternate embodiment of attachment is an elastomeric tip that will fit in the neck of the reservoir opening replacing the original tip. The elastomeric properties will again allow the male end of the elastomeric tip to seal to the reservoir opening and remain in place to perform its function, similar to a cork in a bottle. In summary the elastomer can be utilized to adapt over and into an existing reservoir as required but the function of the device will be unaltered. In some circumstances the reservoir may be continuous with the device, for example when the device is configured to be compatible with single use eye droppers constructed of silicone. Some of these elastomers may have intrinsic antimicrobial properties.

Further, the elastomeric material preferably is configured with liquid repellent properties, such as hydrophobicity and oleophobicity, which repel excess residue from the internal and external structures when application and usage is taking place. The elastomeric surface can be configured as needed with a micro or nanosurface to alter the liquid surface interface and thereby augment function.

After the dropper device is secured over the existing dropper bottle or reservoir an effective seal is obtained sufficient that gentle force can be applied to the sidewalls of the reservoir to push fluid down a flexible elastomeric conduit.

The flexible elastomeric conduit provides a conduit to convey the liquid away from the reservoir toward the end of dispensing termini of the apparatus. In a preferred embodiment, the liquid will then enter a conveyance space (collapsed tube) that is fully closed at rest by elastomeric recoil. A conceptual illustration of this concept is a cut made though a tube that has been filled with silicone. In the resting or native state the silicone is collapsed and the cut may not be visible yet when liquid is pressurized at one end it opens allowing liquid to flow through and immediately collapses and seals shut in the absence of pressure. The collapsed tube is of varying length and will serve the user in allowing control while dispensing by placing a slight resistance to the flow of liquid out of the reservoir. As pressure is applied at the reservoir the liquid will leak through this collapsed tube and form a drop. The collapsed tube allows the drop to form slowly providing the user control of the speed with which the liquid comes out of the tip and forms the drop. Having a controlled formation of the drop provides an important difference from the operation of a typical eye dropper bottles which allow the liquid to jet out with little force. This cut or slit will reseal (collapse) the tube so no flow take place when the reservoir is depressurized. This resealing or collapsing is is caused by providing the slit being formed in resiliently collapsible body, allowing it to reseal and this feature will serve to reduce or eliminate reflux into the reservoir.

When pressure is applied at the reservoir this formerly collapsed conduit will be forced open and liquid will flow through it. After the reservoir is relieved of pressure the elastomer will recoil and the collapsed tube will shut. Liquids may have as high viscosity such as paste can also be transmitted through this system. Once the quantity of liquid formed at the end of the conveyance system is large enough it will start to move, propelled by gravity. The length of the conveyance structure consisting of a dynamic passageway operated by elastomeric recoil will highly influence the overall length of the device and can be adapted according to use needs. The geometric properties including but not limited to the length of the conduit can be adjusted to allow liquid dispensing at variable speed and variable force input required at the reservoir. A short tube may be needed to make a more compact device that travels well for instance.

Liquid is forced into the conveyance system by compressing and increasing the pressure in the bottle or reservoir as is standard practice. Once an eye drop is dispensed and the force of compression is released then suction is generated at the reservoir. This suction at the reservoir will cause the collapsed elastomeric passageway to adhere with more force preventing any substance beyond the conveyance system terminal from going back into the reservoir. Factors which will reduce contamination include, but not limited to, a relatively narrow collapsed conveyance system, elastomeric recoil of the conveyance system which is collapsed at a resting state and the negative pressure at the reservoir created by the void from dispensed liquid.

In a preferred embodiment one or more structures near the end of the tube will contact the droplet as it forms or shortly after it has finished forming or after it falls or otherwise moves aided by gravity. The liquid falls a very short distance aided by gravity similar to a standard eye dropper bottle. The liquid will encounter and adhere to these structures after it begins to fall and effectively "guide it" to the desired location. Surface tension properties of the liquid along with adhesion of the liquid to the elastomer will facilitate transfer to the suspension frame. Liquid will cling to the structures at the dispensing end (or tip) of the apparatus both while moving and while at rest utilizing adhesion principles. Adhesion is when liquid droplets cling to solid structures such as early morning dew on plants. Cohesion causes the liquid droplet to remain together with the configuration of the device be such that this property is employed to allow the device to function. This is known colloquially as surface tension.

This device is configured in multiple parameters not limited to geometry, surface composition and microstructure to accomplish this purpose. Furthermore the configuration of the components can be manipulated to change the functionality of the device by directly harnessing the physics of liquid properties. For instance the geometry and surface properties of the tip could be changed to enhance the liquid "bead up" and allow user visualization and transfer from the device tip to the eye. There are innumerable configurations that can be employed to slightly alter the function of the device but the basic principle is that the device is configured to utilize these forces to hold the liquid quantity and then facilitate easy and safe transfer the ocular surface. Once the droplet reaches the terminal geometric configuration of the device it will be temporarily suspended for application.

The configuration at the end of the collapsed conveyance system can be manipulated to dispense the desired volume of the droplet or liquid. This will largely be determined by the nipple or the nozzle at the end of the conveyance system that is closed under a resting state. Nozzles with a finer tip will produce a smaller droplet and larger more blunt ones will produce a larger volume droplet. This will be similar to what one would find under the cap of an off the shelf eye dropper only in this device it is placed on the end of the improved conveyance system. Moreover, the liquid volume formation apparatus will have geometric configuration to keep the volume of liquid together until it reaches critical mass to move.

A preferred embodiment of this device is that it will break off a preconfigured volume of liquid and separate it from the liquid in the reservoir and transfer it to a portion of the liquid to a location on the end of the device that will hold it for application on the surface of the eye. This device contains embodiments that allow for controlled liquid dispensing and subsequent transmission of the liquid to suspension frame where the liquid is contained by harnessing the cohesion and adhesion properties of a liquid volume or droplet. The liquid or droplet will then be brought in very close approximation to the moisturized surface of the eye, and it will spontaneously transfer to the eye. The unique geometry of this device makes temporary suspension of the droplet possible.

Gravity will preferably provide some or all of the force for movement of the liquid droplet between the nozzle (also known as the terminal of the conveyance structures) and the holding apparatus on the end. The configuration of the structures between the terminal of the conveyance system and the suspension frame are designed to facilitate optimal transfer. This will keep drops from prematurely falling away from the entire apparatus. The connecting structures may vary in distance from each other in size, shape, length, surface area, material composition and geometric configuration but are not limited to these mentioned variances. A conceptual illustration is a water droplet moving along a string or other fine structure that has a partially vertical orientation instead of falling and taking a route exactly parallel to gravity.

In a further embodiment a conveyance system is provided that is immediately adjacent to the suspension frame. With this configuration the liquid is conveyed through the conveyance system the liquid volume to be dispensed will not move appreciably and will not require the force of gravity because it does not move. The liquid will simply collect in the temporary containment area which is immediately continuous with the end of the collapsed conveyance system. This area will have a configurable geometry which can be manipulated not limited to shape, size, surface properties or material properties. Further because this area contains the liquid as it is dispensed to will only hold a finite volume which is dictated by but not limited to its structure. The volume of liquid will not be propelled by gravity in this variation of the device. It will still dose a specific quantity of liquid dictated by what the temporary holding area can hold based off adhesion and cohesion properties of the liquid.

The configuration of the various embodiments, namely the connecting structures and temporary suspension area will be such that once volume of liquid has lodged in or on this geometric configuration it will remain in place unless at the intended transfer. The spatial and dimensional orientation at the end of the device will be configured such that a droplet will easily move aided gravity to the very end. By altering the surface area, size, shape material, composition, geometric configuration and other variables of the temporary suspension area it will securely hold specified volume of liquid until brought into close contact with another liquid surface (the eye surface in most cases). The physical properties of but not limited to capillary action and contact angle will facilitate liquid cohesion and adhesion while the liquid is moving from the terminal of the conveyance system to the temporary suspension region. These same physical properties will be utilized as the liquid is transferred to the ocular surface. The droplet will remain suspended even if the device is moved along all axes, even vertical. It is understood by the inventor that there may be many alternative embodiments of the area that contains the droplet or liquid volume as is transferred to the surface of the eye. A wide variety of geometric configurations and surface properties can be utilized to provide a temporary suspension of a small liquid quantity, and the breadth of the claims includes a multitude of configurations, unless expressly limited in scope.

There has always been an important consideration of maintaining sterility or at least trying to minimize contamination of the reservoir containing eye dropper fluids. Once the volume of liquid separates off at the at the nozzle or end of the tubular conveyance system the geometric and other physical properties are configured to facilitate one way movement of the liquid to the temporary suspension area.

The disclosed concepts can be utilized as an attachment for overlaying and extending the components of a commercially available eye drop bottle, as a removable tip that attaches to an eye drop bottle or even as an integrally formed end of the eye drop bottle. In an embodiment that overlays the pre-existing nipple, the device preferably utilizes an elastic material that allows constricts on the preexisting nipple, such as at the base of the nipple and extending upward toward the tip of the nipple. This constriction provides for a continuous conduit from the reservoir, through the preexisting nipple, and out the tip of the attachment to the suspension section.

The integrally positioned piece can fit and secure in the neck of an eye dropper bottle conforming to the existing structures of the reservoir and neck. Not limited to, but in many cases the elastomer will conform around and inside of the circumferential opening of the reservoir to retain the attachment in place. The device is also configured to utilize elastomeric and conjoined nonelastomeric materials found in the native eye dropper bottle. For example, the elastomeric base is lodged in the opening and be held to the geometry of the reservoir by the elastomeric properties. Optimally it would be designed to fit under the same cap that came with the reservoir and just place the plastic dispensing apparatus on most reservoirs.

The eye dropper devices disclosed herein will help to reduce or eliminate the need for positioning of the head of the person or animal receiving the drops. Since the droplet will remain on the end also understood to be the temporary suspension area no matter what orientation the device is in, the droplet can be brought in close approximation to the eye in any orientation. This will eliminate the need for a person to tilt the head back. Whereas the force of gravity aided the transference of the volume of liquid to the temporary suspension area the properties of said structure overcome gravity and hold the liquid fast.

The end of the apparatus or temporary suspension domain is configured such that the surface area, geometry and physical make up will "attract" the droplet enough it will stay in place. The end may also have deep groves (the temporary suspension area) in the end to create favorable contact angles with the droplet surface and thus hold it better. When brought near the wet surface of the eye it will "jump" or readily transfer by cohesion forces between the liquid applied and the liquid on the eye. Because the droplet can be applied in all orientations and the device is configured to have minimal profile a user could instill it under direct observation, for instance application could take place using the wall mirror in the bathroom under direct vision of the user.

If the droplet did fall back toward the opening at the end of the terminal conveyance system, the geometry will preferably be configured such that it will be directed toward the periphery of the device. This will minimize the chance for contamination of the reservoir.

The device described herein may also have color or other configurations not limited to geometry, materials, or structure which will allow users to easily visualize the droplet when suspended on the end of the device. This may include using the refractive properties of the liquid, or other refractive materials integrated into the device such as silicone or fiber optic materials but not limited to these materials. For instance, the temporary suspension area may contain but not limited to a color which will be refracted through a transparent volume of liquid serving assist the user in indicating the presence of liquid in this area.

The eye drop applicator and or attachment can further include a removable cap intended to protect the device from the environment and thereby reduce the risk of contamination. This cap could also facilitate placement of the device on a bottle by giving the user some extra leverage. Alternatively, the device could be removed from the original reservoir and the original cap reapplied.

In a preferred embodiment of this device the intrinsic elastomeric properties will be used to secure existing device to the reservoir. An elastomeric material will be utilized to form an overlay over the portion that was covered by the original cap, and this includes the threads on most eye dropper bottles. Moreover, the overlay portion that encapsulates the threads of most bottles is configured to be inverted to facilitate easy application. An illustration of this is having an undersized silicone component relative to the dispensing apparatus of the eye dropper bottle which would stretch to fit over the native dispensing terminus, threads, and neck of the original bottle. This elastomeric material would then overlay and grip to the native threads or other structures on an eye dropper bottle thus securing it well. The device is preferably configured to be one continuous elastomer from the suspension frame the base that secures it to the other components of the reservoir. The elastomeric properties and geometric configuration this device will readily adapt to different sizes and configurations of reservoir.

In the following description and the figures, like elements are identified with like indications materials and the use of "e.g." "etc." and "or" indicates non-exclusive alternatives without limitation unless otherwise noted. The use of "including" means "including but not limited to" unless otherwise noted.

DETAILED DESCRIPTION OF THE INVENTION

FIG. 1a illustrates a first embodiment of an eye dropper cap being configured to suspend a droplet of liquid for placement into a user's eye. The cap has an end piece configured to be place over or on to an eye dropper reservoir. In certain embodiments disclosed herein the eye dropper tip attachment is configured to be positioned over a preexisting eye dropper tip of a typical eye dropper reservoir and tip apparatus, typically called an eye dropper dispenser bottle. In the depicted cap, the tip 4 of the attachment has a geometry configured to retain a drop of liquid that is dispended from the reservoir through the neck of the applicator and onto the tip. The end geometry uses a first arcuate segment 8 that extends from a first side of the tip 10 to an opposing point 12 across the diameter of the tip 14. Fluid dispenses from the tip 10 and drops into the suspension location defined by the first cross component 8 and a generally perpendicular component 16. Preferably, the device is utilized when the eye dropper are inverted. Alternatively, if sufficient capillary action is present, the liquid can bleed on top of the tip. The materials of the cross sections 8, 16 are typically formed of a soft component such that the user can touch the material to the user's eyes and have the material give so as to not damage an eye.

FIG. 1b illustrates the magnified image of the tip as shown around Circle B in FIG. 4. FIG. 1c illustrates the tip having internal components shown with dashed lines. The first void 18 in the applicator body 3 is positioned over a rim of an eye drop bottle. The tip of the eye dropper bottle is positioned into the second void 20. Pressure on the reservoir bottle causes fluid to travel through the tip, as illustrated by broken line 22 into the void defined by the tip 10 and the cross members 8, 16.

Figure 1F:
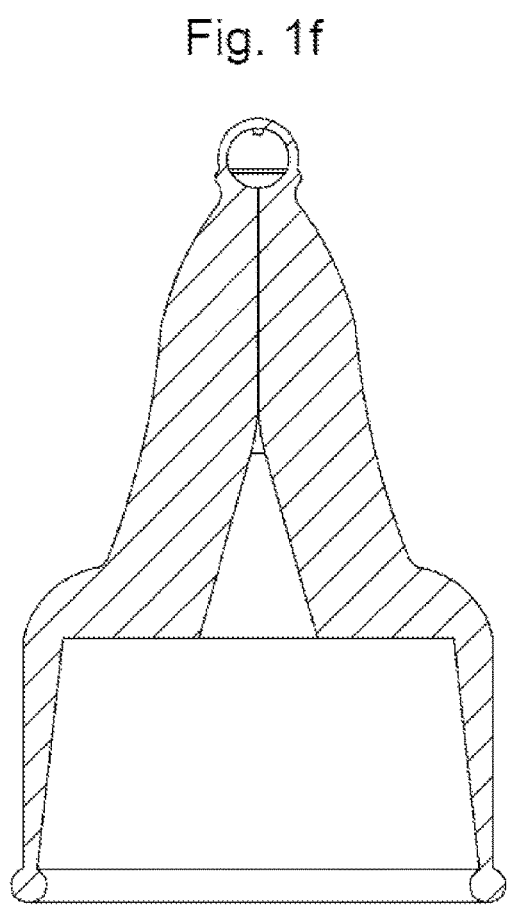
FIG. 1f is a section view along line A of FIG. 1e.

FIGS. 1d, 1e, 1f illustrate alternative views of the tip of FIGS. 1a-1c. FIG. 1f illustrates a cross sectional along line A of FIG. 1e illustrating the internal components also shown in FIG. 1c.

Figure 2A:
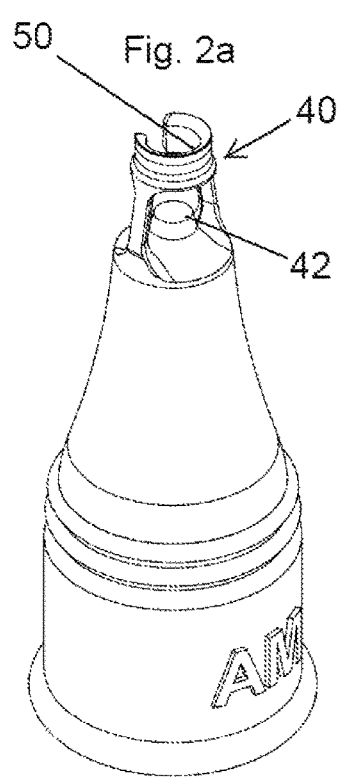
FIG. 2a is a perspective view of a second embodiment of an eye dropper dispenser attachment configured to suspend a drop of liquid for placement in a user's eye.
Figure 2B:
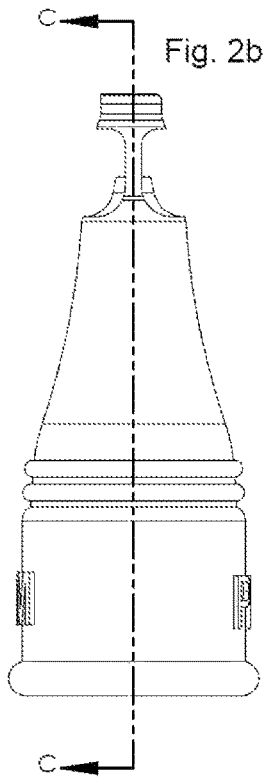
Figure 2C:
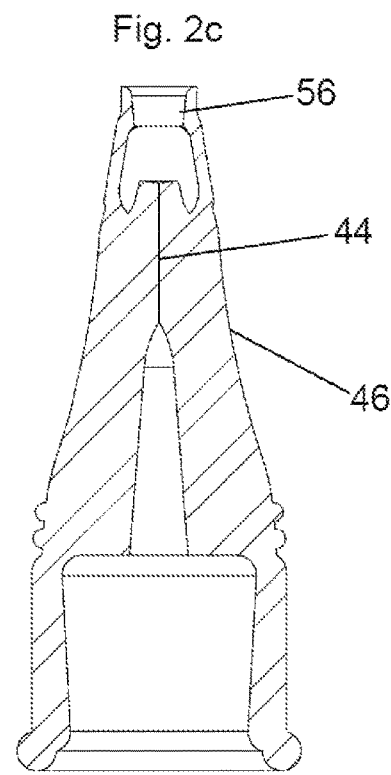
FIG. 2c is a section view of the embodiment of FIGS. 2a-2b along line C of FIG. 2b.
Figure 2D:
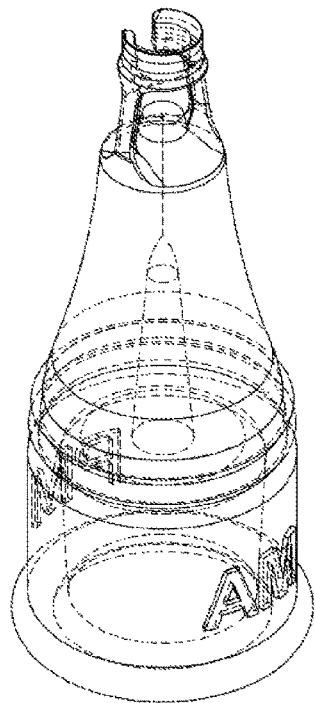
FIG. 2d is a perspective view illustrating the internal configuration of the embodiment of FIGS. 2a-2c.
Figure 2E:
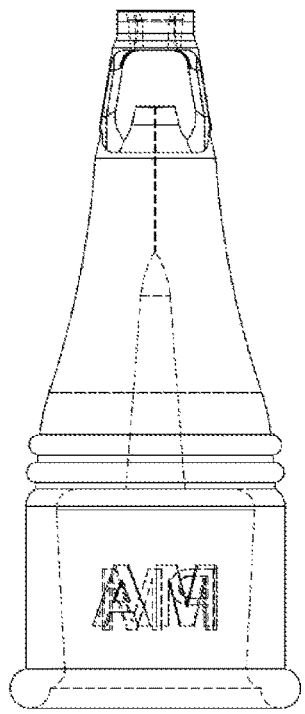
FIG. 2e is an isometric view illustrating the internal configuration of the embodiment of FIGS. 2a-2d.
Figure 2F:
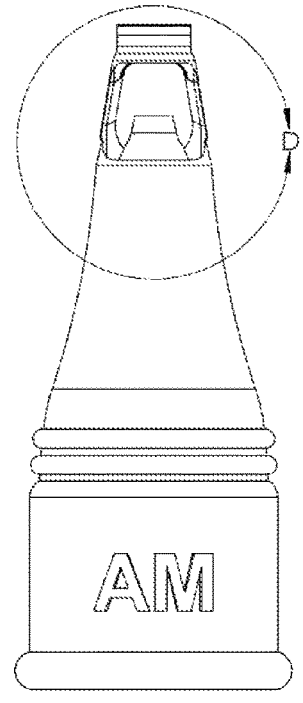
FIG. 2f is an isometric view of the embodiment of FIGS. 2a-2e.
Figure 2G:
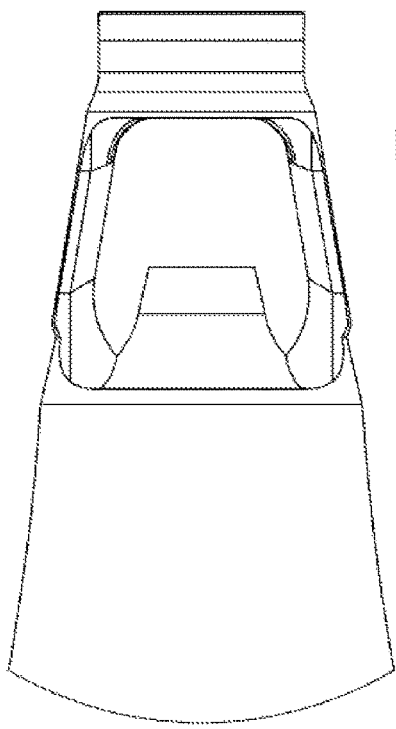
FIG. 2g is a detail view of the embodiment of FIGS. 2a-2f along detail line D.
Figure 2H:
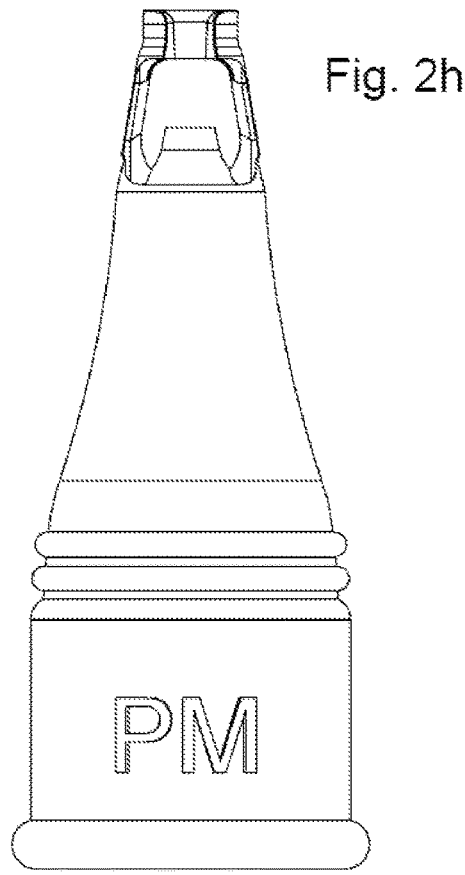
FIG. 2h is an isometric view of the embodiment of FIGS. 2a-2g.
Figure 3A:
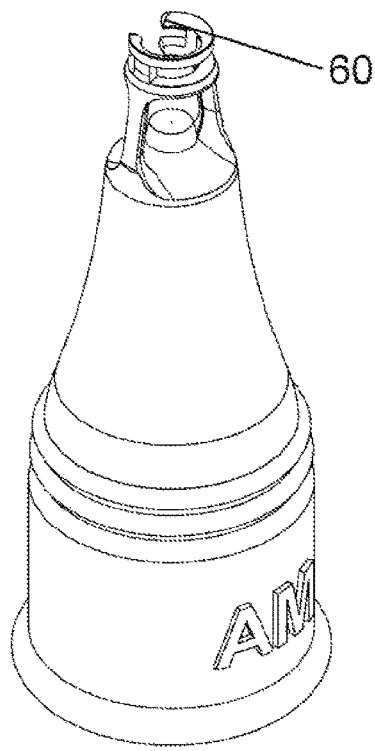
FIG. 3a is a perspective view of a third embodiment of an attachment for an eye dropper dispenser.
Figure 3B:
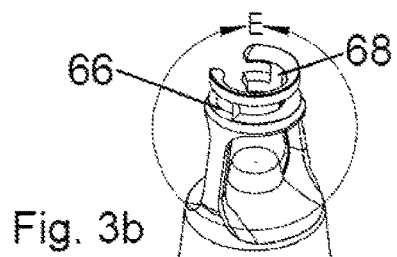
FIG. 3b is the perspective view of FIG. 3a illustrating detail line E.
Figure 3C:
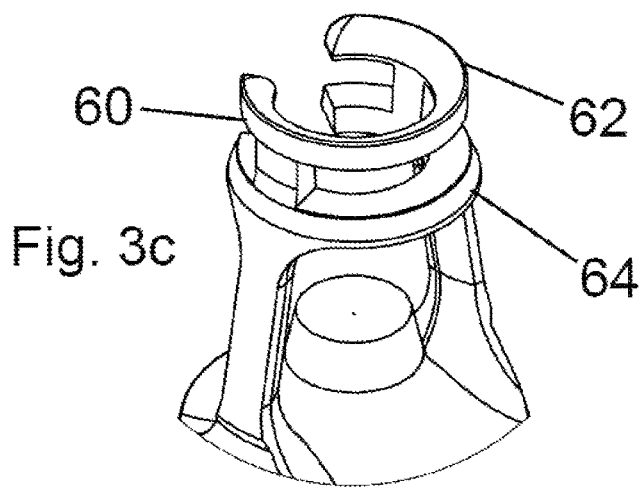
FIG. 3c is a detail view of the tip of the attachment of FIG. 3a-3b along line E of FIG. 3b.
Figure 3D:
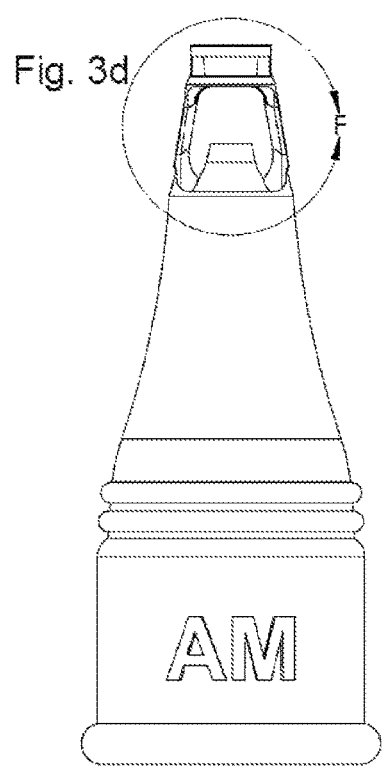
FIG. 3d is an isometric view of the embodiment shown in FIGS. 3a-3c illustrating detail line F.
Figure 3E:
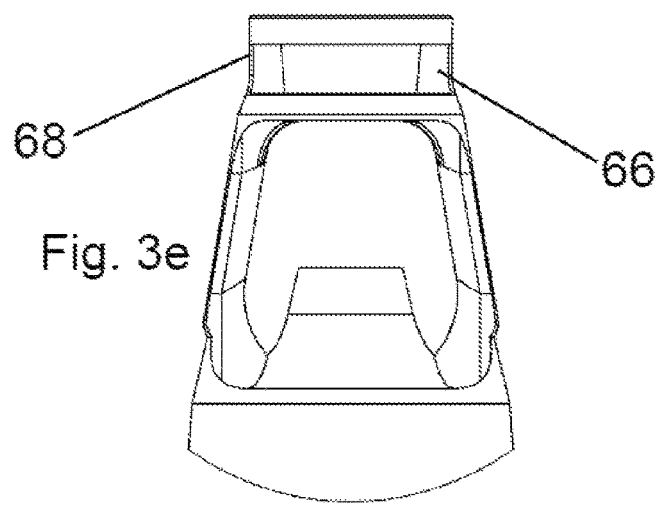
FIG. 3e is a detail view within detail line F of FIG. 3d.
Figure 4A:
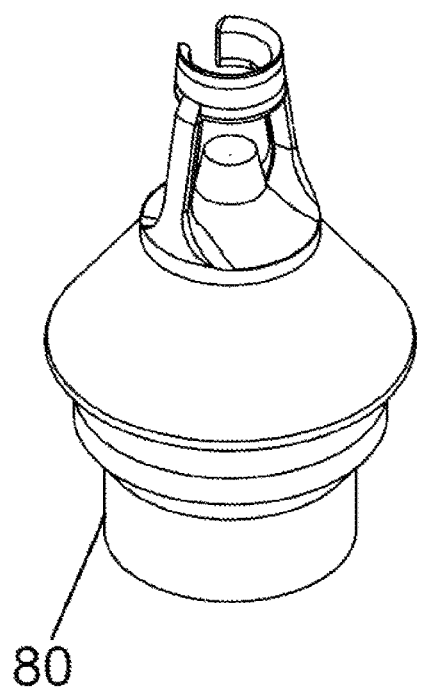
FIG. 4a is a is a fourth embodiment of an attachment for an eye dropper dispenser configured for positioning within a neck of an opening to the reservoir.
Figure 4B:
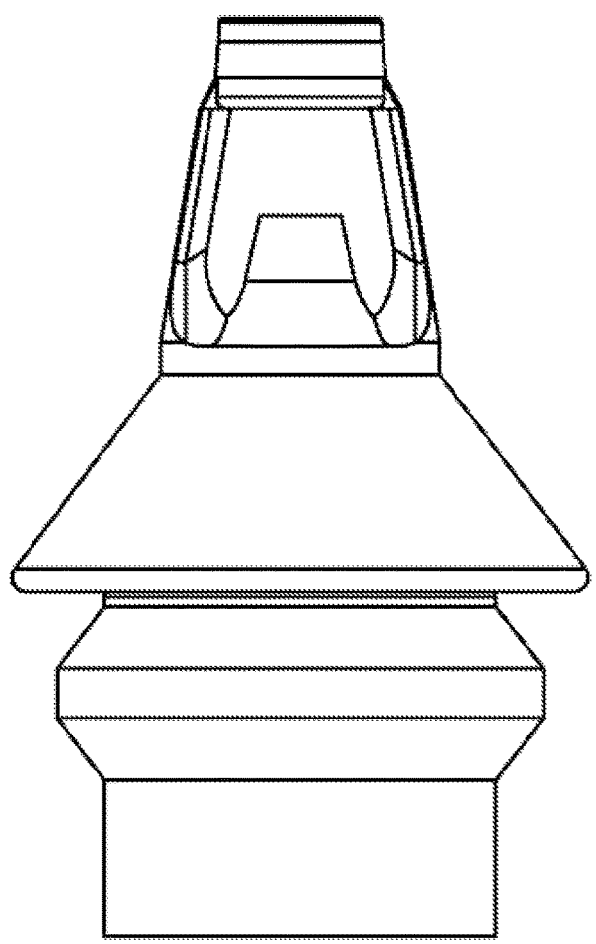
Figure 4C:
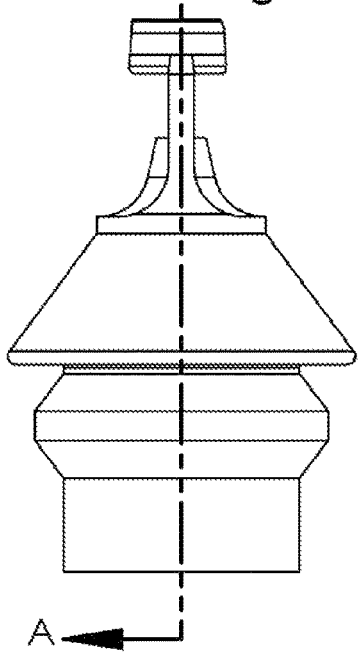
Figure 4D:
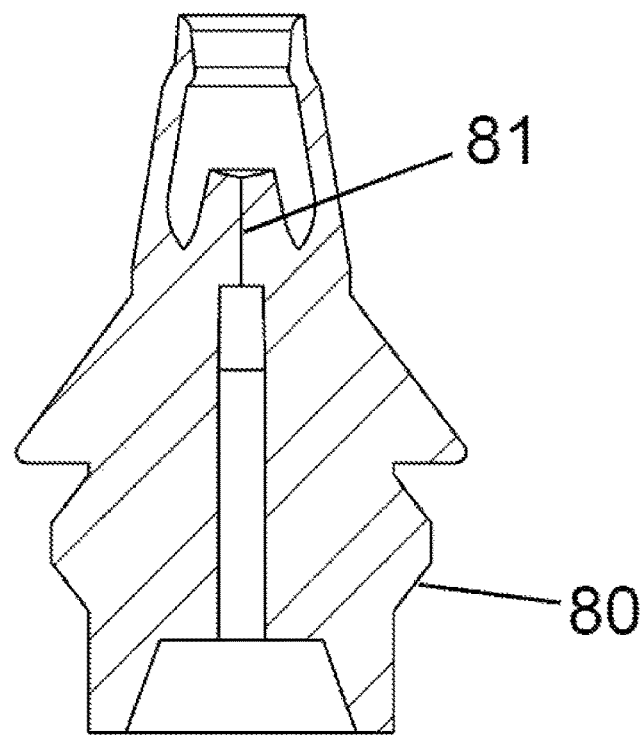
FIG. 4d is a section view along line A of FIG. 4c.

FIGS. 2a-2h illustrate a second embodiment of a tip for positioning on an eye dropper dispenser similar to the embodiment of FIG. 1, the depicted tip has an interior component illustrated in FIGS. 2c, 2d, 2e that illustrates how the tip is positioned over the preexisting tip of the eye dropper bottle. The depicted embodiment has an alternate tip section 40. The tip section receives fluid from orifice 42 that dispenses material from the lumen 44 within the neck 46 of the dispenser tip. The tip is configured such that a drop of liquid forms from the orifice in space 48. The dispenser tip and reservoir are preferably inverted when the liquid drop because large enough, it drops under force of gravity into the suspension frame 50. The suspension frame 50 is illustrated with a slight taper 56 within the suspension frame, such that the drop of liquid is retained within the device.

FIG. 3 illustrates a third embodiment of an eye dropper tip attachment. The embodiment is similar to the previous figures but utilizes a different geometry on the tip section 60. The depicted embodiment utilizes two partial rings 62, 64 held apart by the support section 66, 68. FIGS. 4a-4d illustrate an alternative embodiment of the device of FIGS. 2a-2h which is configured to replace the tip of a preexisting eye dropper bottle. The base 80 is configured of insertion into the opening of a preexisting eye dropper bottle after removing the tip. Alternatively, the depicted embodiment can be manufactured along with a reservoir and can be provided commercially with a reservoir integral with the dispenser tip.

Figure 5A:
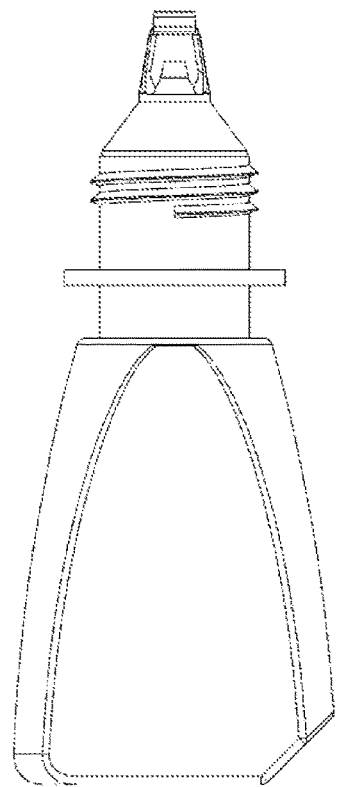
FIG. 5a is an isometric view of an embodiment of the attachment of FIGS. 4a-4d attached by inserting the base of the attachment into the opening of the neck of an eye drop reservoir.
Figure 5B:
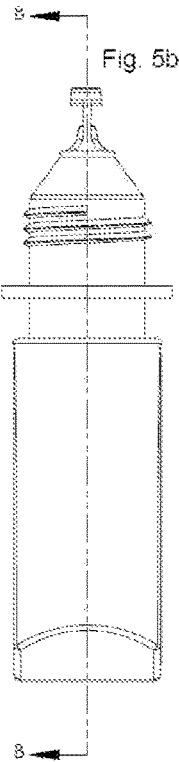
FIG. 5b is a side isometric view of the attachment and reservoir of FIG. 5b.
Figure 5C:
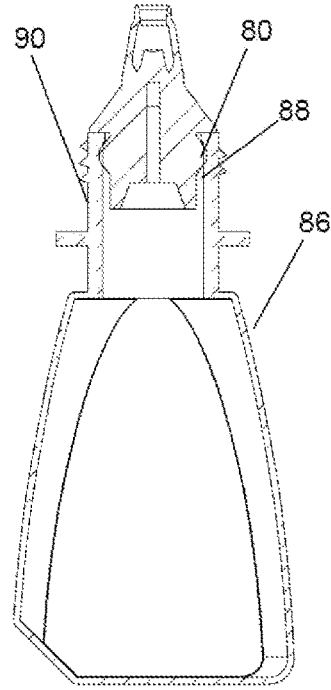
FIG. 5c is a detail view of the attachment and reservoir of FIG. 5c along line SB of FIG. 5b.
Figure 6A:
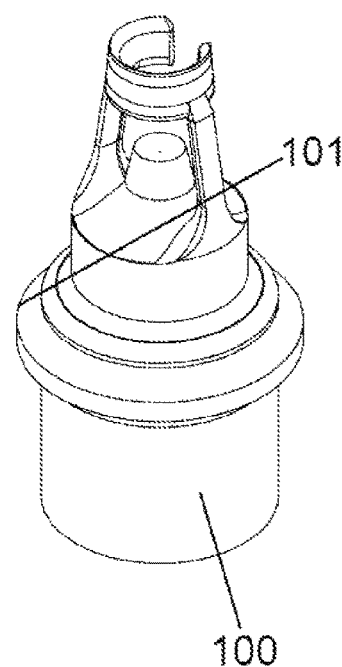
FIG. 6a illustrates a perspective view of an alternate embodiment configuration of an attachment configured for insertion into the opening of a neck of an eye dropper reservoir.
Figure 6B:
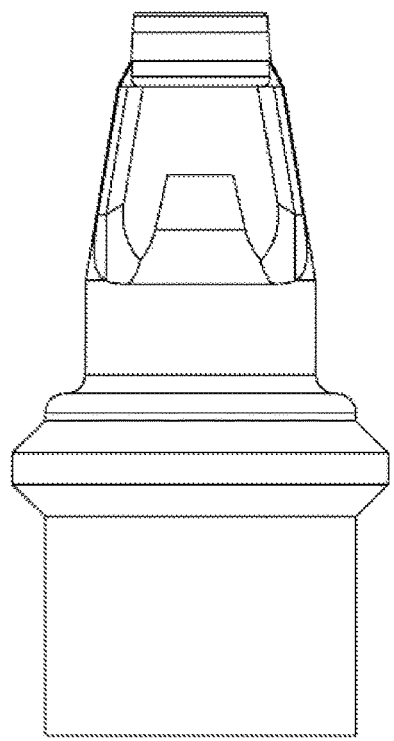
Figure 6C:
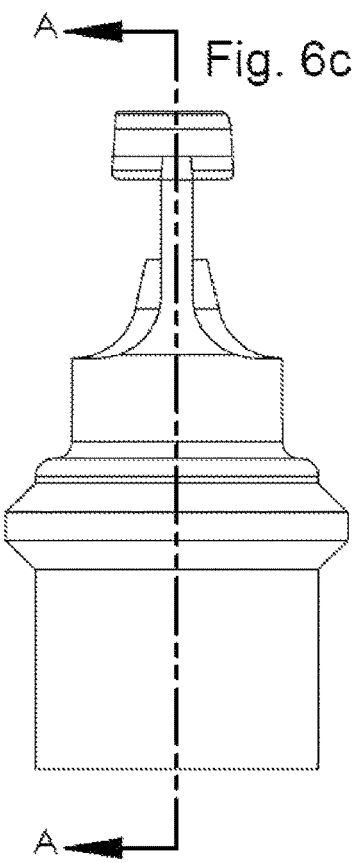
FIG. 6c illustrates an isometric view of the embodiment of FIGS. 6a-6b.
Figure 6D:
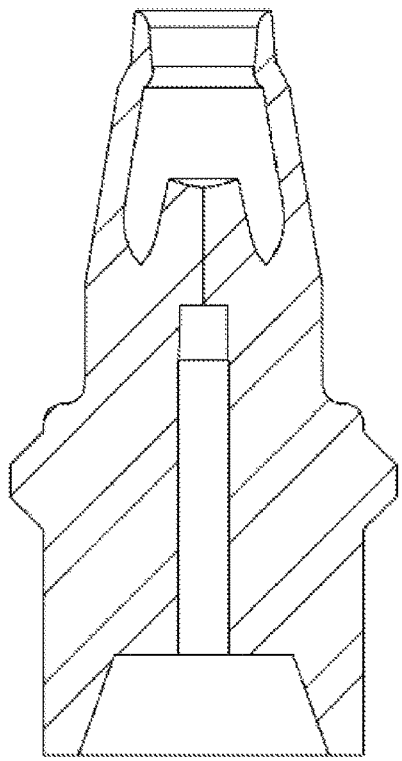
FIG. 6d illustrates a detail view of the embodiment of FIGS. 6a-6c along line A of FIG. 6c.
Figure 6E:
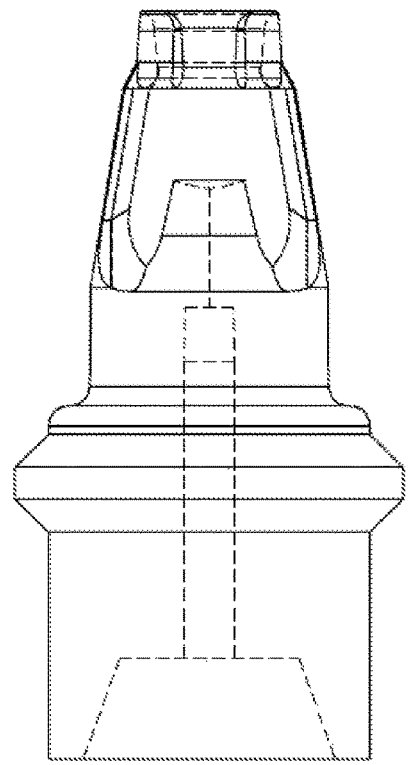
FIG. 6e illustrates an isometric view illustrating the internal configuration of the embodiment of FIGS. 6a-6d by dashed lines.
Figure 6F:
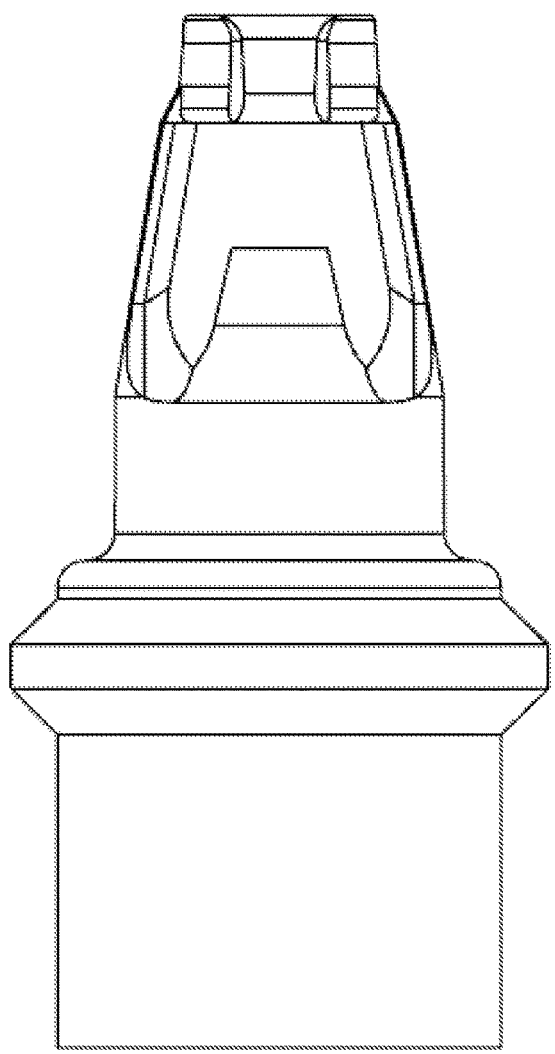
FIG. 6f illustrates an isometric view of the embodiment of FIGS. 6a-6f.
Figure 7A:
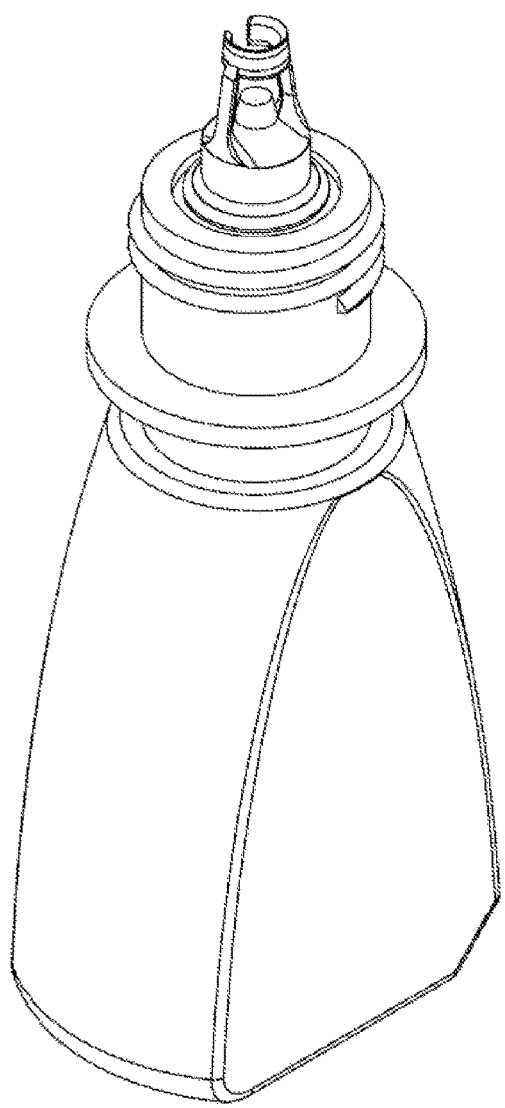
FIG. 7a illustrates a perspective view of the embodiment of FIGS. 6a-6f positioned within the opening defined by the neck of the eye drop reservoir.
Figure 7B:
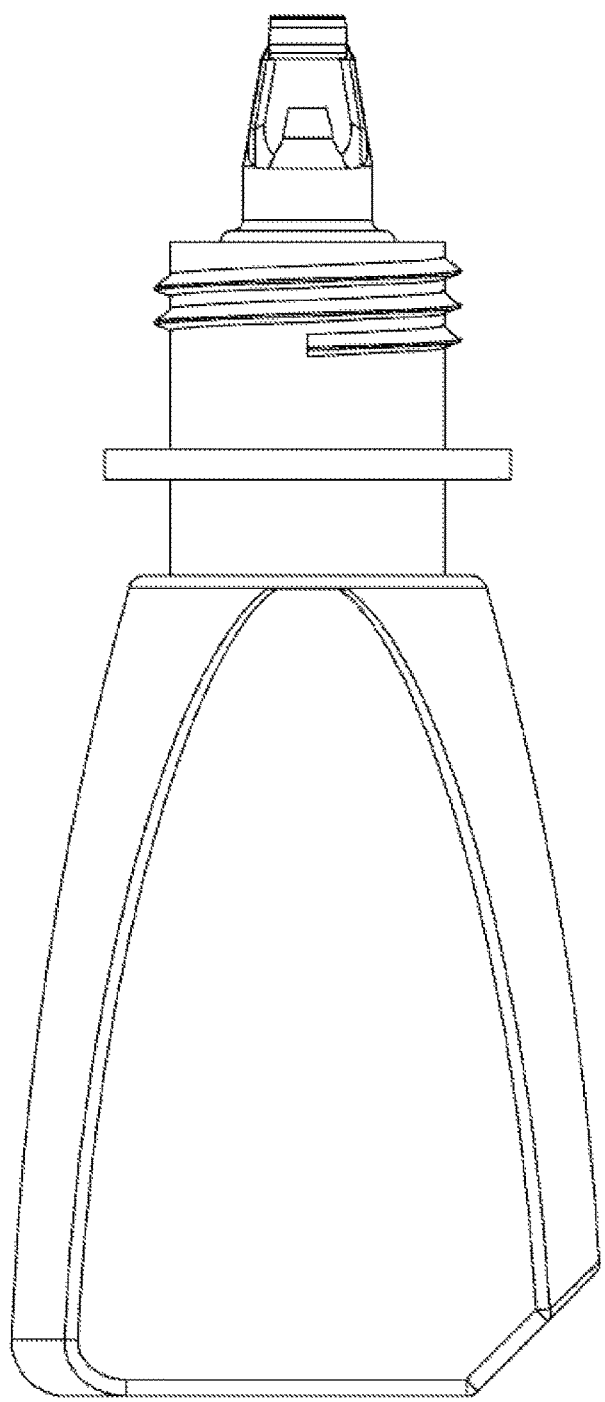
FIG. 7b illustrates an isometric view of the embodiment of FIGS. 6a-6f positioned within the opening defined by the neck of the eye drop reservoir.
Figure 7C:
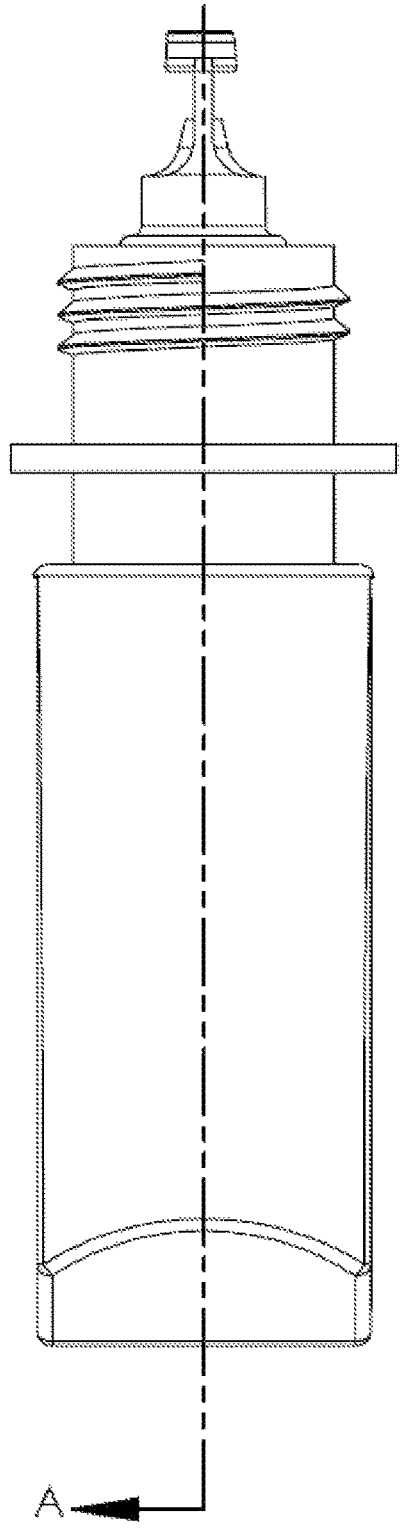
FIG. 7c illustrates a side isometric view of the embodiment of FIGS. 6a-6f positioned within the opening defined by the neck of the eye drop reservoir.
Figure 7D:
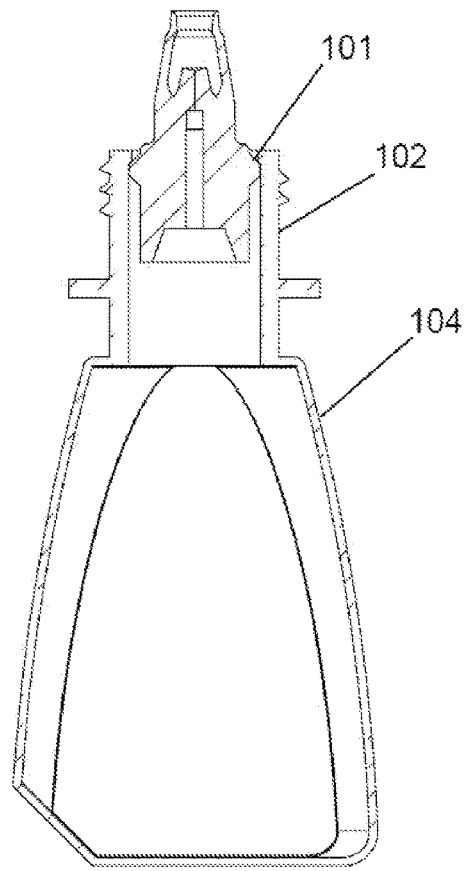
FIG. 7d illustrates a section view along line A of FIG. 7c.
Figure 8A:
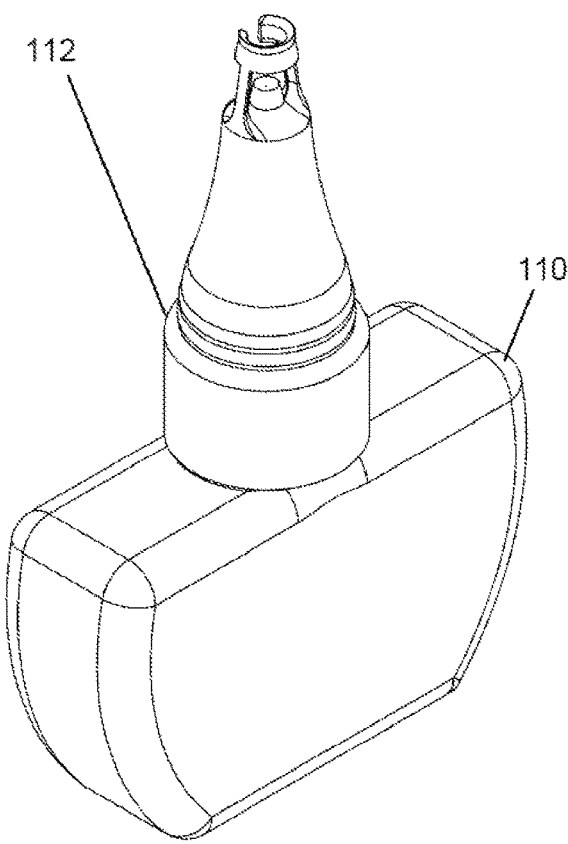
FIG. 8a illustrates a perspective view of the embodiment of FIGS. 2a-2c positioned over the preexisting dispenser tip of a smaller eye drop dispenser.
Figure 8B:
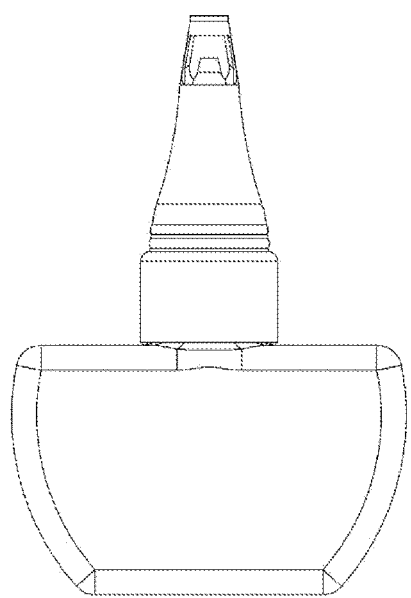
FIG. 8b illustrates an isometric view of the embodiment of FIGS. 2a-2c positioned over the preexisting dispenser tip of a smaller eye drop dispenser.
Figure 8C:
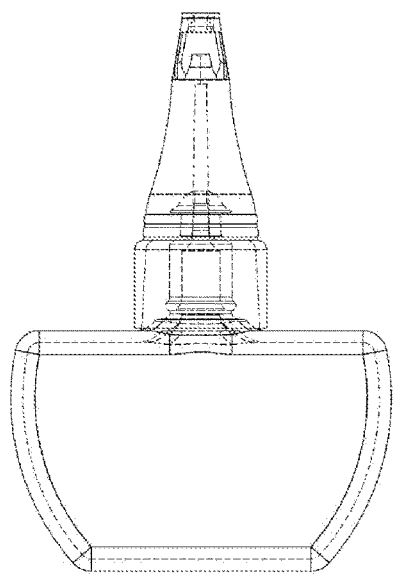
FIG. 8c illustrates the isometric view of the embodiment of FIGS. 2a-2c positioned over the preexisting dispenser tip of a smaller eye drop dispenser with the internal configuration of the assembly shown in dashed lines.
Figure 8D:
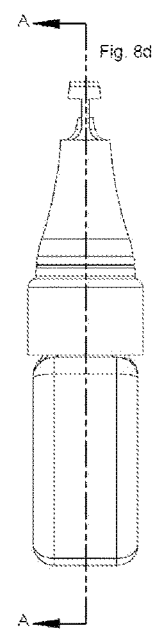
FIG. 8d illustrates a side isometric view of the embodiment of FIGS. 2a-2c positioned within the opening defined by the neck of the eye drop reservoir.
Figure 9B:
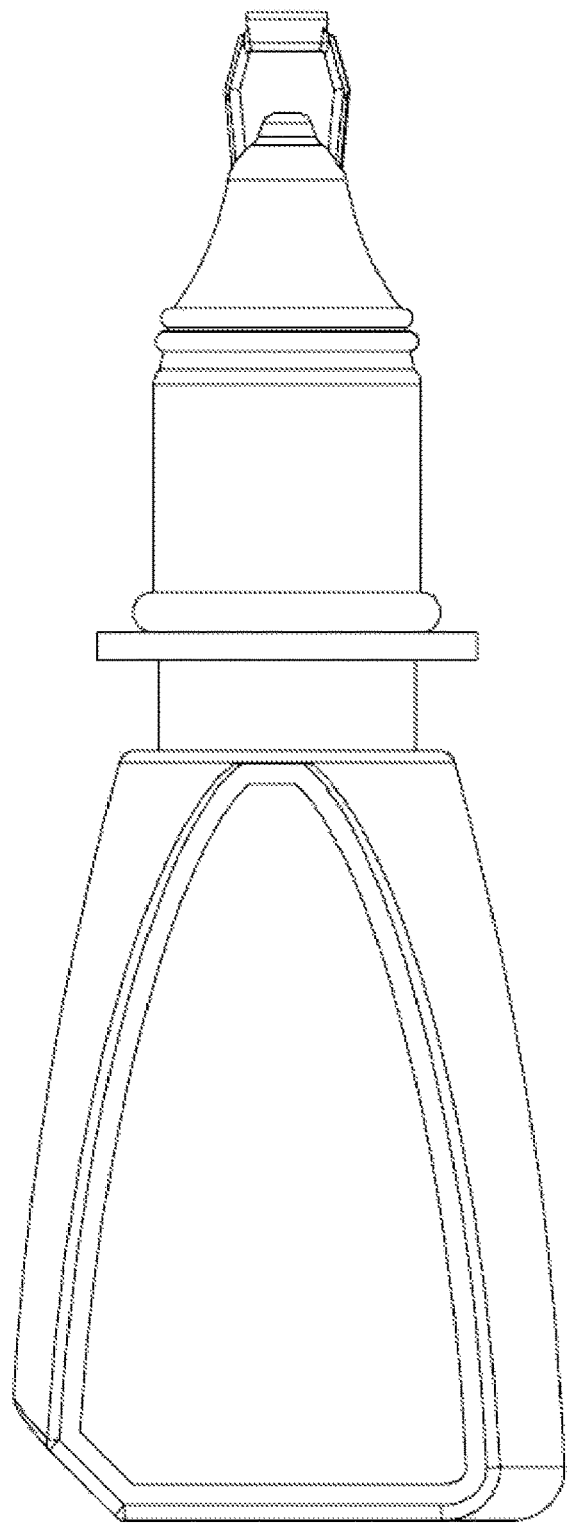
Figure 9C:
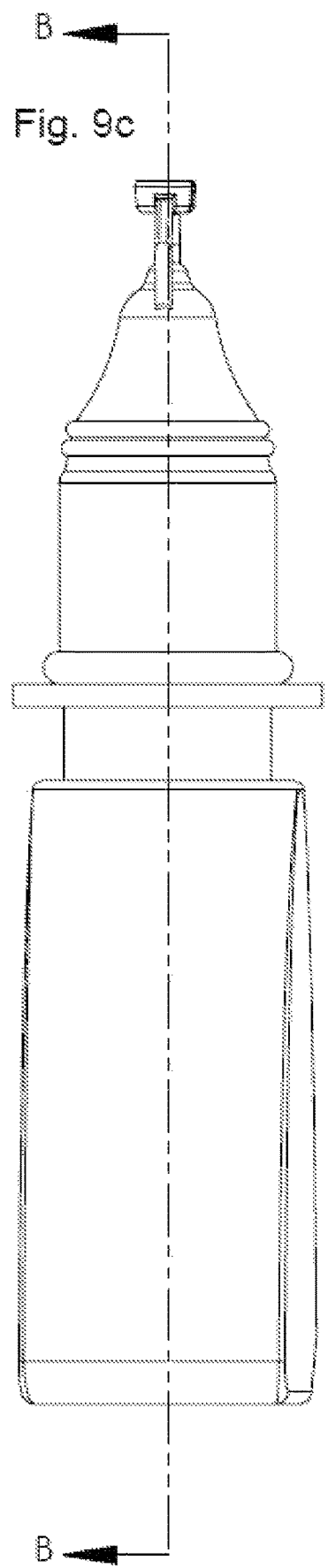
FIG. 9c illustrates a side isometric view of the assembly of FIG. 9b.
Figure 11A:
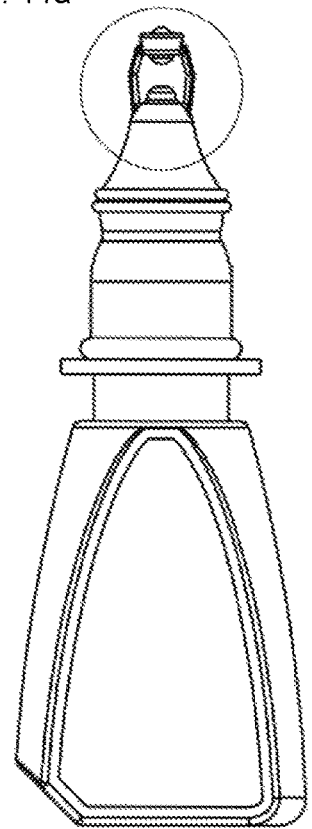
FIG. 11a illustrates an isometric view of a reservoir and dropper assembly in a vertical position.
Figure 11B:
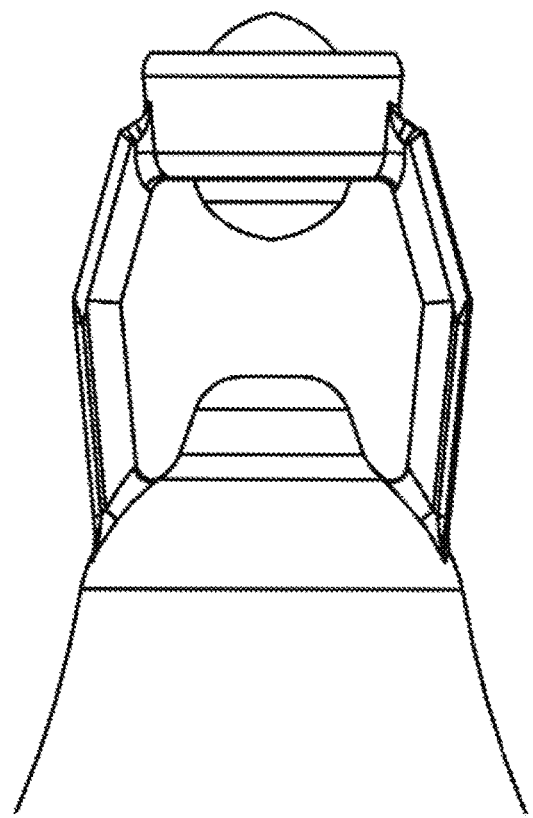
Figure 11C:
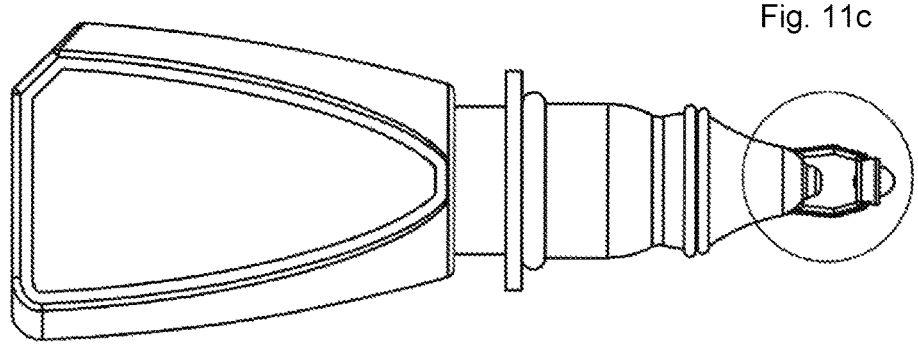
FIG. 11c illustrates an isometric view of a reservoir and dropper assembly in a horizontal position.
Figure 11D:
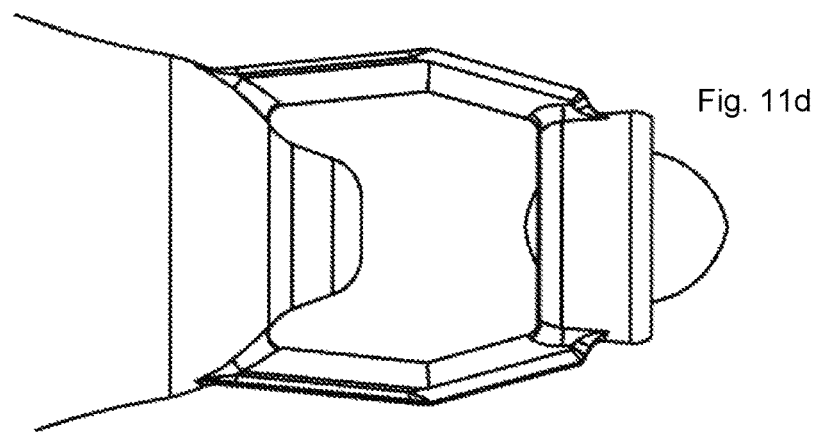
FIG. 11d illustrates a detail view of the dispensing end of the reservoir and dispensing attachment of FIG. 11c.
Figure 11E:
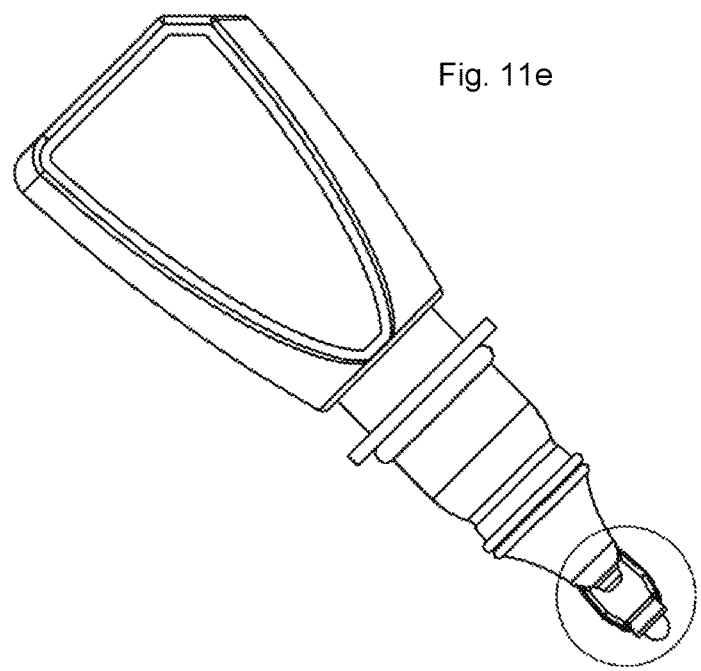
FIG. 11e illustrates an isometric view of a reservoir and dropper assembly in an angled or tilted position.
Figure 11F:
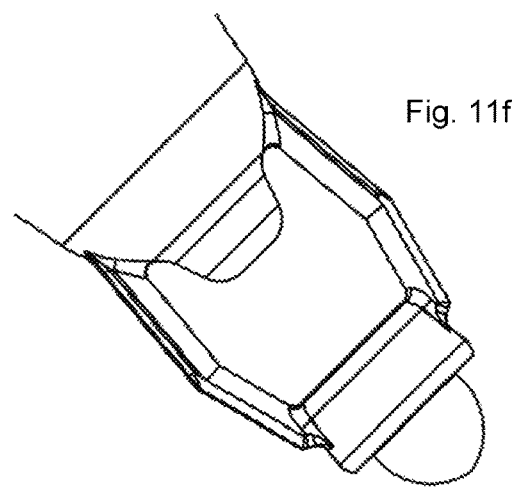
FIG. 11f illustrates a detail view of the dispensing end of the reservoir and dispensing attachment of FIG. 11e.

FIG. 5a illustrates the embodiment of FIGS. 4a-4d connected to a reservoir 86. The base 80 has been inserted into the opening defined by the eye dropper reservoir neck 90. This assembly is typically inverted with the reservoir 86 squeezed by a user causing fluid droplet down the neck of the dispenser to the attachment. FIGS. 6a-6f illustrate the tip embodiment of FIGS. 2a-2h configured for connection to replace a tip of a preexisting eye dropper reservoir or to be integral with a reservoir provided commercially. FIG. 7a-7d illustrate the embodiment of FIGS. 6a-6f positioned in a neck 102 of a preexisting eye dropper reservoir 104. The flange 101 provides a liquid tight seal within the neck.

FIGS. 8a-8e illustrate the embodiment of FIGS. 2a-2c positioned onto a smaller eye-dropper reservoir 110. The dispenser tip 112 is positioned over a tip and orifice of the dispenser reservoir, with the dispenser tip 112 providing a channel 160 through which liquid travels from the reservoir to the orifice 164 at the end of the dispensing bottle. Force applied to the reservoir causes liquid to travel from the reservoir internal cavity 156 through the reservoir tip, into the channel 160, with pressure causing the liquid to travel through the sealing tip 162 and out the orifice. The sealing tip is configured such that pressure of the liquid in the tip causes the opposing sides to separate enough to allow liquid to exit the orifice and to form a droplet in airspace 168 below the suspension frame 170 preexisting dispenser tip of the bottle. Preferably this is constructed by a piercing action through a uniform silicon structure by a needle or other small diameter object.

FIGS. 9a-9d illustrate a further embodiment of a dispenser tip 180 positioned over a dropper tip 182 attached to a reservoir 184. The function is similar to that of prior disclosed embodiments, with the dispenser tip providing a fluid tight connection with the reservoir dropper tip. The internal geometry of the dispenser tip can be configured in a variety of structures for mating engagement with a dropper tip of a reservoir, or alternatively for mating engagement direct with the dropper reservoir. The silicon construction of the dispenser tip has allowed the dispenser tip to provide a sealing connection to the preexisting drop dispenser at least around the neck 183 of the preexisting tip, and more preferably around the frustoconical tip 185 of the preexisting dispenser.

FIGS. 10a and 10b illustrate an alternate embodiment of the tip section of the apparatus. In the depicted embodiment the suspension frame 206 can be configured in a variety of geometrical configurations to retain the liquid in a suspended state. The support arms 202, 204 are positioned to support the suspension frame in a spaced apart relationship to the dispensing orifice 208 of the apparatus. As discussed above, this spaced apart relationship allows the liquid to bead in space 210 until the volume and/or weight of the forming droplet drops or otherwise transfers from the space to the suspension frame 206. Typically this dispensing of liquid occurs in an inverted position, with the reservoir and dispenser apparatus then inverted for use. A user then holds the device such that the suspension frame near the eye, and the surface tension of the drop causes the drop to migrate to the eye of the user. The suspension frame and support arms are preferably configured to deflect if the suspension frame touches the eye to avoid damaging the user's eye. The deflection configuration can be by using a resilient material that bends with a small amount of force applied, or to mechanically deflect along axis Z as shown in FIGS. 10*a* and 10*b*, as well as horizontally (not shown) to protect the user's eye. In the depicted embodiment the support arms illustrated 201, 203 are formed with bends or elbows 202, 204 that bend to allow the compression of the suspension frame toward the orifice.

FIG. 10*c* illustrates a user applying a drop of liquid 224 to the user's eye 220. The drop has been suspended in the apparatus (as shown in further detail in FIGS. 11*a*-11*f*). The reservoir and applicator assembly 226 is positioned such that the suspension frame 228 of the applicator is held proximate to the eye such that the suspended drop touches the eye. The surface tension of the drop causes the drop to migrate to the user's eye. The support arms 230, 232 are configured to deflect to reduce potential for eye harm or damage if the user inadvertently contacts the applicator to the eye.

FIGS. 11*a*-11*f* illustrate the retention of an eye drop in the suspension frame of the dispensing tip. The internal geometry and material configuration retains the drop suspended in the dispenser as the apparatus is rotated between vertical up right positions to vertical downward. This property allows the drop to be dispensed from the orifice in an inverted position to fall or otherwise travel across the void between the orifice and the suspension frame, and to be retained on the tip. The assembly of the dispensing tip and reservoir can then be rotated toward upright, with the eye drop maintained in the tip. The eye drop can then be dispensed into an eye by positioning the tip proximate an eye such that the eye drop touches the eye.

Still other features and advantages of the presently disclosed and claimed inventive concept(s) will become readily apparent to those skilled in this art from the following detailed description describing preferred embodiments of the inventive concept(s), simply by way of illustration of the embodiments contemplated by carrying out the inventive concept(s). As will be realized, the inventive concept(s) is capable of modification in various obvious respects all without departing from the inventive concept(s). Accordingly, the drawings and description of the preferred embodiments are to be regarded as illustrative in nature, and not as restrictive in nature.

What is claimed is:

1. An eye drop dispenser, said dispenser comprising: a reservoir, said reservoir configured to retain an eye drop liquid, said reservoir comprising an opening for flow of a liquid into and out of said reservoir; an eye drop applicator comprising:
    a body extending away from said reservoir, said body comprising a base and a dispenser tip, said base being connected to said eye drop reservoir, said dispenser tip positioned at a distal end of said body from said base;
    said body defining an internal fluid passageway positioned within said body and providing fluid connection between a dispenser tip orifice in said dispenser tip and said reservoir;
    at least one support arm extending from said body to a suspension frame such that said suspension frame and said body are in a spaced apart arrangement forming a drop forming space such that when said applicator and reservoir are inverted a liquid drop forms from liquid dispensed from said tip orifice in the drop forming space until the liquid drop is of sufficient size to either fall from said drop forming space to said suspension frame or to transfer from said drop forming space to said suspension frame by capillary action;
    said suspension frame defining a top opening and a bottom opening, wherein said bottom opening is configured for receiving the liquid drop dispensed from said dispenser tip, wherein said suspension frame is configured to retain said drop in suspension on said suspension frame using the surface tension of the liquid and adhesion properties of the liquid such that a user can transfer the drop to a user's eye by placing the eye drop proximate to the user's eye, wherein said suspension frame and arm are configured to deflect from contact with the user's eye.

2. The eyedrop dispenser of claim 1, wherein said reservoir comprises a neck defining said orifice, wherein said base is positioned within said neck.

3. The eyedrop dispenser of claim 1, wherein said reservoir comprises a neck defining said orifice, wherein said base is positioned around said neck.

4. The eyedrop dispenser of claim 1, wherein said reservoir comprises a reservoir eyedrop dispenser tip, wherein said body is positioned around said reservoir eyedrop dispenser tip.

5. The eyedrop dispenser of claim 1, wherein said eye drop applicator comprises two arms extending between said tip and said suspension frame.

6. The eyedrop dispenser of claim 1 wherein said arm are configured to bend by an elbow of said arm.

7. The eyedrop dispenser of claim 1 wherein said suspension frame comprises a series of ridges configured to suspend said eyedrop.

8. The eyedrop dispenser of claim 1 wherein said suspension frame comprises a circular shape.

9. The eyedrop dispenser of claim 8 comprising two support arms positioned on opposite sides of said circular shape.

10. The eyedrop dispenser of claim 8 wherein said circular shape comprises an incomplete circle.

11. The eyedrop dispenser of claim 1 where said top opening is wider than said bottom opening.

12. The eyedrop dispenser of claim 10 wherein said suspension frame comprises two spaced apart partial rings.

13. The eyedrop dispenser of claim 4 wherein said body comprises an elastic material.

14. The eyedrop dispenser of claim 1 wherein said internal fluid passageway is configured to prevent reflux of material dispensed from said dispenser tip into said internal fluid passageway.

15. The eyedrop dispenser of claim 1 wherein said body is resiliently collapsible such that said internal fluid passageway is closed in the absence of pressure on said reservoir.

16. An eyedrop applicator attachment for an eye drop reservoir, said eyedrop applicator attachment comprising:
    a body extending between a base and a dispenser tip, said base being configured for attachment to an eyedrop reservoir, said dispenser tip positioned at a distal end of said body from said base;
    said body defining an internal fluid passageway positioned within said body and configured to provide fluid connection between a dispenser tip orifice in said dispenser tip and in the reservoir;

at least one support arm extending from said body to a suspension frame such that said suspension frame and said body are in a spaced apart arrangement forming a drop forming space such that when said applicator tip and reservoir are inverted a liquid drop forms from liquid dispensed from said tip orifice in the drop forming space until the liquid drop is of sufficient size to either fall from said drop forming space to said suspension frame or to transfer from said drop forming space to said suspension frame by capillary action;

said suspension frame defining a top opening and a bottom opening, wherein said bottom opening is configured for receiving the liquid drop dispensed from said dispenser tip, wherein said suspension frame is configured to retain said drop in suspension on said suspension frame such that a user can transfer the drop to a user's eye by touching a portion of said drop to the user's eye through said top opening.

\* \* \* \* \*